(12) United States Patent
Pearson et al.

(10) Patent No.: US 8,535,306 B2
(45) Date of Patent: Sep. 17, 2013

(54) ABLATION DEVICES AND METHODS OF USING THE SAME

(75) Inventors: Robert Pearson, San Jose, CA (US); Lewis Isbell, Los Altos, CA (US); Valerie Douglass, Mountain View, CA (US)

(73) Assignee: AngioDynamics, Inc., Latham, NY (US)

( * ) Notice: Subject to any disclaimer, the term of this patent is extended or adjusted under 35 U.S.C. 154(b) by 1117 days.

(21) Appl. No.: 11/935,075

(22) Filed: Nov. 5, 2007

(65) Prior Publication Data

US 2009/0118727 A1 May 7, 2009

(51) Int. Cl.
*A61B 18/14* (2006.01)

(52) U.S. Cl.
USPC .................. 606/41; 606/32; 606/33; 606/34; 606/35; 606/49

(58) Field of Classification Search
USPC ..................... 606/32–35, 41, 45–52
See application file for complete search history.

(56) References Cited

U.S. PATENT DOCUMENTS

| | | | |
|---|---|---|---|
| 4,401,124 A | 8/1983 | Guess et al. | |
| 4,735,205 A | 4/1988 | Chachques et al. | |
| 4,869,259 A | 9/1989 | Elkins | |
| 4,907,589 A | 3/1990 | Cosman | |
| 4,977,894 A | 12/1990 | Davies | |
| 5,080,660 A | 1/1992 | Buelna | |
| 5,273,524 A | 12/1993 | Fox et al. | |
| 5,342,357 A | 8/1994 | Nardella | |
| 5,383,466 A | 1/1995 | Partika | |
| 5,458,597 A | 10/1995 | Edwards et al. | |
| 5,490,521 A | 2/1996 | Davis et al. | |
| 5,496,314 A | 3/1996 | Eggers | |
| 5,536,267 A | 7/1996 | Edwards et al. | |
| 5,549,112 A | 8/1996 | Cockburn et al. | |
| 5,578,067 A | 11/1996 | Ekwall et al. | |
| 5,599,345 A | 2/1997 | Edwards et al. | |
| 5,605,539 A | 2/1997 | Buelna et al. | |
| 5,683,384 A | 11/1997 | Gough et al. | |
| 5,728,124 A | 3/1998 | Cockburn et al. | |
| 5,792,140 A | 8/1998 | Tu et al. | |
| 5,902,320 A | 5/1999 | Matsutani et al. | |
| 5,919,222 A | 7/1999 | Hjelle et al. | |
| 5,935,123 A | 8/1999 | Edwards et al. | |
| 6,001,096 A | 12/1999 | Bissinger et al. | |
| 6,018,676 A | 1/2000 | Davis et al. | |
| 6,071,280 A | 6/2000 | Edwards et al. | |
| 6,102,907 A | 8/2000 | Smethers et al. | |
| 6,129,726 A | 10/2000 | Edwards et al. | |

(Continued)

FOREIGN PATENT DOCUMENTS

| | | |
|---|---|---|
| EP | 0566725 | 10/1993 |
| EP | 0703756 | 4/1996 |

(Continued)

*Primary Examiner* — Michael Peffley
*Assistant Examiner* — Khadijeh Vahdat
(74) *Attorney, Agent, or Firm* — Peter J. Flora

(57) ABSTRACT

Devices and methods for ablating a selected tissue volume, such as for ablating tumor, are disclosed. In certain embodiments, the ablation devices include a low-conductivity, tissue-piercing tip, an adjustment mechanism for selectively adjusting the length of an exposed portion of the electrode, for producing ablation volumes of desired geometry. In other embodiment, the methods allow the adjustment of the length of the exposed electrode portion be carried out by moving an insulative sleeve along the electrode.

7 Claims, 11 Drawing Sheets

(56) References Cited

U.S. PATENT DOCUMENTS

| | | |
|---|---|---|
| 6,391,027 B1 * | 5/2002 | Farin et al. .................. 606/45 |
| 6,471,698 B1 | 10/2002 | Edwards et al. |
| 6,641,580 B1 | 11/2003 | Edwards et al. |
| 6,663,624 B2 | 12/2003 | Edwards et al. |
| 6,936,048 B2 * | 8/2005 | Hurst .......................... 606/41 |
| 7,150,744 B2 | 12/2006 | Edwards et al. |
| 2003/0078573 A1 * | 4/2003 | Truckai et al. ............... 606/41 |
| 2003/0097130 A1 * | 5/2003 | Muller et al. ................ 606/41 |
| 2003/0212394 A1 * | 11/2003 | Pearson et al. .............. 606/41 |
| 2004/0158239 A1 * | 8/2004 | Behl et al. ................... 606/41 |
| 2004/0210215 A1 * | 10/2004 | Okada .......................... 606/45 |
| 2005/0107781 A1 * | 5/2005 | Ostrovsky et al. ........... 606/41 |
| 2005/0203503 A1 | 9/2005 | Edwards et al. |
| 2005/0277918 A1 * | 12/2005 | Shah et al. .................. 606/41 |
| 2006/0122593 A1 * | 6/2006 | Jun .............................. 606/41 |

FOREIGN PATENT DOCUMENTS

| | | |
|---|---|---|
| EP | 0723467 | 7/1996 |
| EP | 0830095 | 3/1998 |
| PE | 0693955 | 1/1996 |

* cited by examiner

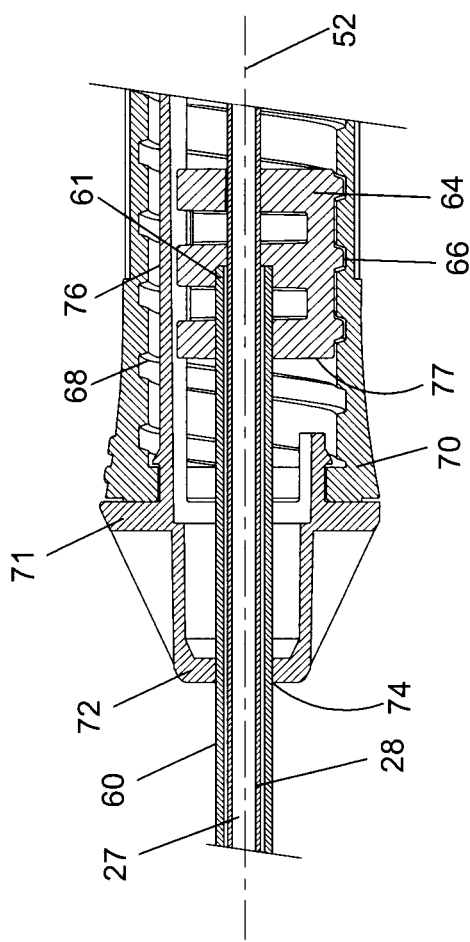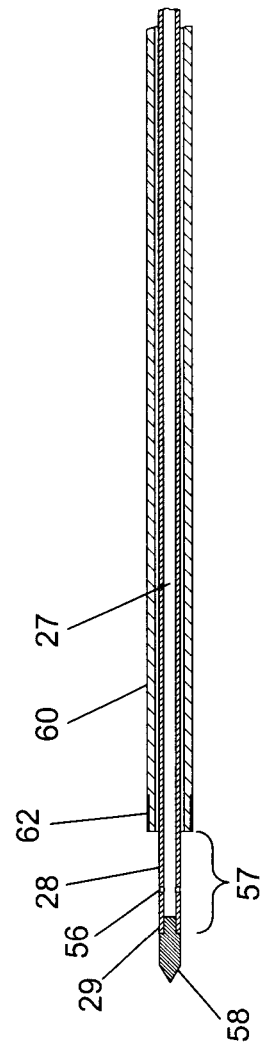

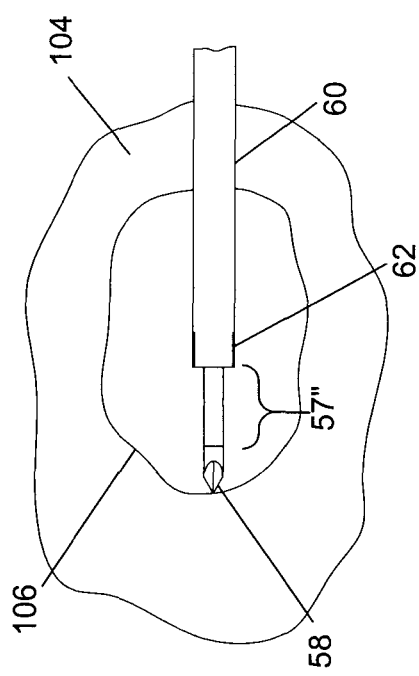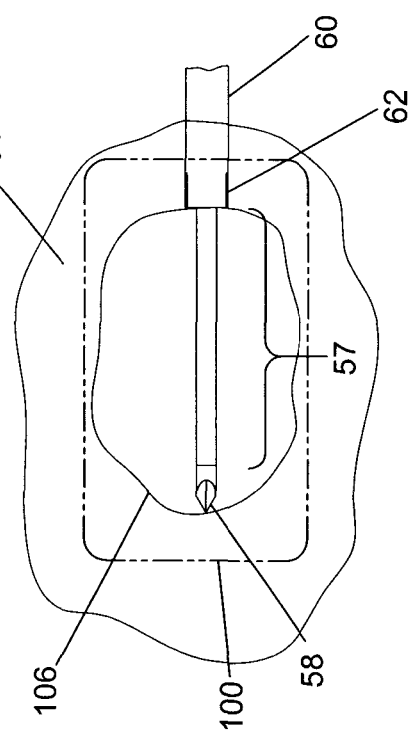

ABLATION DEVICES AND METHODS OF USING THE SAME

FIELD OF THE INVENTION

The present invention relates to ablation devices and methods of using such devices for creating selected volume ablations in a tissue.

BACKGROUND

Current open procedures for tissue ablation (e.g., tumor destruction and/or removal) are disruptive and cause considerable damage to healthy tissue. In tumor treatments, a physician must exercise care during a surgical procedure to avoid cutting the tumor in a manner that creates seeding of tumor cells, resulting in metastasis. Also, some patients are not eligible for open surgical techniques due to their general state of health. In recent years, products have been developed to minimize the traumatic nature of traditional surgical procedures; however, ablation surgery is by no means a trivial procedure.

Chemotherapy and radiation therapy are alternatives to open surgical procedures for treating tumors, but they expose healthy tissues and sometimes the entire body to toxic chemicals. Side effects from chemotherapy and radiation therapy are well known and include hair loss, loss of appetite, and malaise. Moreover, such chemical treatments often fail to achieve complete destruction of tumors at doses acceptable to the patient, ultimately leading to recurrence and the need to repeat the procedure.

An alternative to conventional surgical techniques and chemical treatment is the use of hyperthermia for tissue destruction and/or removal through necrosis. Treatment methods for applying tissue-damaging heat to target tissues such as tumors include the use of direct contact radio-frequency (RF) applicators, inductively coupled RF fields, microwave radiation, and a variety of simple thermal conduction techniques. These techniques are often referred to collectively as thermal ablation techniques.

SUMMARY OF THE INVENTION

In one embodiment, an ablation device for ablating a selected tissue volume in a patient contains a handle, a hollow, tubular electrode having a blunt distal end and a distal end coupled to the handle, a low-conductivity, tissue-piercing, tip securely coupled to the distal end of the electrode, and an insulative sleeve extending over a major proximal portion of the electrode such that the electrode is exposed to a target tissue of the patient only between the sleeve and the tip. When RF energy is applied to the exposed portion of the electrode, it is effective to ablate the selected tissue volume. The axial position of a distal end of the sleeve along the electrode may be adjustable for selection of different ablation volumes. The electrode may have one or more openings along the exposed portion for delivery of fluid to the target tissue. The exposed portion may be ultrasonically reflective or radio-opaque, or either one, or both, of the low-conductivity tip and a distal end of the sleeve may be ultrasonically reflective or radio-opaque.

In another embodiment, an ablation device for ablating a selected tissue volume in a patient contains a handle coupled to an electrode having a central axis, an insulative sleeve coaxially adapted over a portion of the electrode and is rotatable about the central axis, a nut through which the electrode passes, the nut being coupled to the sleeve and rotatable about the central axis, and an adjustment member through which the electrode passes, the adjustment member being movably coupled to the nut through an arm, and the nut being rotatable about the central axis. Rotation of the adjustment member about the central axis is capable of rotating the nut about the central axis and consequently moving the sleeve along the electrode. The adjustment member may be coupled to the handle. The nut may be positioned within the handle. The handle may be transparent or contains at least one window through which at least a portion of the nut is visible. The handle may further contain indicia for identifying an axial length of a portion of the electrode not covered by the sleeve. The electrode may have one or more openings along the exposed portion for delivery of fluid to the target tissue. The exposed portion may be ultrasonically reflective or radio-opaque, or either one, or both, of the tip and a distal end of the sleeve may be ultrasonically reflective or radio-opaque.

In another embodiment, an ablation device for ablating a selected tissue volume in a patient contains an electrode having a proximal end and a distal end coupled to a handle, a tissue-piercing tip carried on the distal end of the electrode, and an insulative sleeve extending over a region of the electrode and terminating at a distal end proximal to the distal end of the electrode, such that the electrode is exposed between the sleeve and the electrode distal end. The length of the exposed portion of the electrode may be detectable by virtue of a differential radio-opacity or ultrasound reflectivity between the exposed portion of the electrode and the tip and the sleeve defining the distal and proximal ends of the exposed portion, respectively. The electrode may have one or more openings along the exposed portion for delivery of fluid to the target tissue. The exposed portion may be ultrasonically reflective or radio-opaque, or either one, or both, of the tip and a distal end of the sleeve may be ultrasonically reflective or radio-opaque.

In another embodiment, an ablation device for ablating a selected tissue volume in a patient contains an electrode having a single portion exposed to a target tissue, the exposed portion adjoins, on both a distal end and a proximal end, low-conductivity materials. The exposed portion may provide a spheroidal electric field when RF energy is applied thereto, with electric strength equally concentrated on both ends thereof. When RF energy is applied thereto, the exposed portion of the electrode may be effective to ablate the selected tissue volume such that the selected tissue volume has substantial reflective symmetry with respect to a plane of symmetry of the exposed portion that is orthogonal thereto. The selected tissue volume ablated may be substantially spheroidal (e.g., spherical, ellipsoidal, superellipsoidal) or cylindrical. A ratio of the length of the exposed portion to its diameter may be 60:1 or less, such as 30:1 or less, 20:1 or less, preferably 3:1 or greater.

In another embodiment, an ablation device for ablating a selected tissue volume in a patient contains a single ablating electrode having an adjustable exposed portion for RF energy delivery to the target tissue. The ablation device may further comprise a mechanism for adjusting the length of the exposed portion. The length may be adjusted manually by an operator, semi-automatically, or fully automatically (e.g., based on automated analysis of biological imaging data) without an operator's input (optionally allowing an operator to override the automated length adjustment). The length may be adjusted such that its ratio to the diameter of the exposed portion of the ablating electrode is in a range of from 60:1 to 1.5:1. The length of the exposed portion may be defined by the same or different materials having an electric conductivity of $10^{-4}$ mhos/m or less (but are not limited in their thermal conductivity). The distal end of the electrode distal to the exposed portion may be adapted to have a pointed end for tissue piercing, tissue deflection, and/or tissue dilation (e.g., dilation of vessels, ducts, and other tubular tissues).

In another embodiment, devices are disclosed herein, having a means for delivering electromagnetic energy to a target tissue. Non-limiting examples of the energy delivery means include electrically conductive and slender structures (e.g., cannula, tubular structure, solid rod, coil, spring, braided or woven structures) or a portion thereof. The devices have at least one of 1) a means for adjusting the length of the energy delivery means, and/or 2) a means for creating a substantially spheroidal electric field around the energy delivery means. Non-limiting examples of means for the former include structures resembling telescopic antenna, stretchable coils or springs, as well as insulative sleeves coaxially arranged with the energy delivery means. Non-limiting examples of means for the latter include structures formed of low-conductivity materials coupled to or disposed on portions of the energy delivery means. The low-conductivity structure may be fashioned to have a tissue-piercing feature (e.g., a pointed tip), or fashioned to be free of any sharp or pointed tips or edges (e.g., rounded spheroidal or bulleted shapes).

In another embodiment, devices for ablating and/or coagulating tissues using RF energy are disclosed herein, suitable for, for example, percutaneous, laparoscopic, and intraoperative surgical procedures. These devices use a single cannula electrode having a scalable, electrically conductive (i.e., exposed) distal portion, allowing physicians (e.g., interventional radiologists, oncologists, and surgeons) to perform multiple ablations with the same electrode by adjusting the length of the scalable distal portion. The devices are designed to have full track ablation capability, optionally with built-in cool-down capability (e.g., liquid infusion process) after each ablation, and/or optionally be compatible with a biological imaging process (e.g., fitted in a CT-gantry). These devices are capable of ablating a variety of lesions (e.g., soft tissues) under 10 cm in diameter (e.g., 1 cm to 7 cm in diameter). These devices are designed to reduce the need to switch ablation devices during a multiple ablation procedure, and minimize a hospital's need to maintain an inventory of single electrode RF devices of varying sizes.

In another embodiment, a method for ablating a selected volume of a patient tissue includes: imaging the tissue to determine the location and volume of the selected-volume in the patient tissue, inserting an electrode of a single-electrode ablation device into the tissue, substantially along one axis thereof, adjusting the relative axial position of an insulative sleeve on the electrode, to expose a portion of the electrode, such that the exposed electrode portion is substantially coextensive with said selected volume along said axis, and applying energy to the electrode for a period sufficient to ablate the selected volume. The position of the insulative sleeve on the electrode may be adjusted prior to the inserting. The electrode may have a distal end that can be visualized by tissue imaging. The inserting step may include imaging the electrode tip as the electrode is inserted into the tissue. The electrode may have one or more openings along the exposed portion for delivery of fluid to the target tissue. The exposed portion may be ultrasonically reflective or radio-opaque, or either one, or both, of the tip and a distal end of the sleeve may be ultrasonically reflective or radio-opaque. The electrode may include a low-conductivity tip carried on the distal end of the electrode. Application of an RF voltage across the electrode may be effective to produce an ablation volume whose major axis dimension approximates the combined length of the exposed portion of the electrode and the low-conductivity tip.

In another embodiment, a software package stored on a computer-compatible medium is designed to operate and/or facilitate the operation of at least certain aspects of the devices and/or the methods of using such devices. For example, the software integrates and/or analyzes the data collected from the feedback signals (e.g., temperature of the ablating electrode), the biological imaging (e.g., ultrasound, CT, MRI), certain pre-determined parameters, and optionally other information, to determine the most appropriate action to be taken subsequently, and take such action in an automated mode or recommend the action to the prospective operator.

These and other features of the ablation device will be more fully understood when the following detailed description is read in conjunction with the accompanying drawings.

BRIEF DESCRIPTION OF THE DRAWINGS

FIG. 3A is a partial longitudinal cross-sectional view of an ablation device showing an adjustment mechanism;

FIG. 3B shows, in enlarged longitudinal cross-sectional view, the front portion of an electrode;

FIGS. 8A and 8B illustrate steps in practicing an embodiment of the methods in which the length of the exposed portion of electrode is adjusted once the electrode has been positioned in a target tissue.

DETAILED DESCRIPTION

I. Definitions

Figure 1:
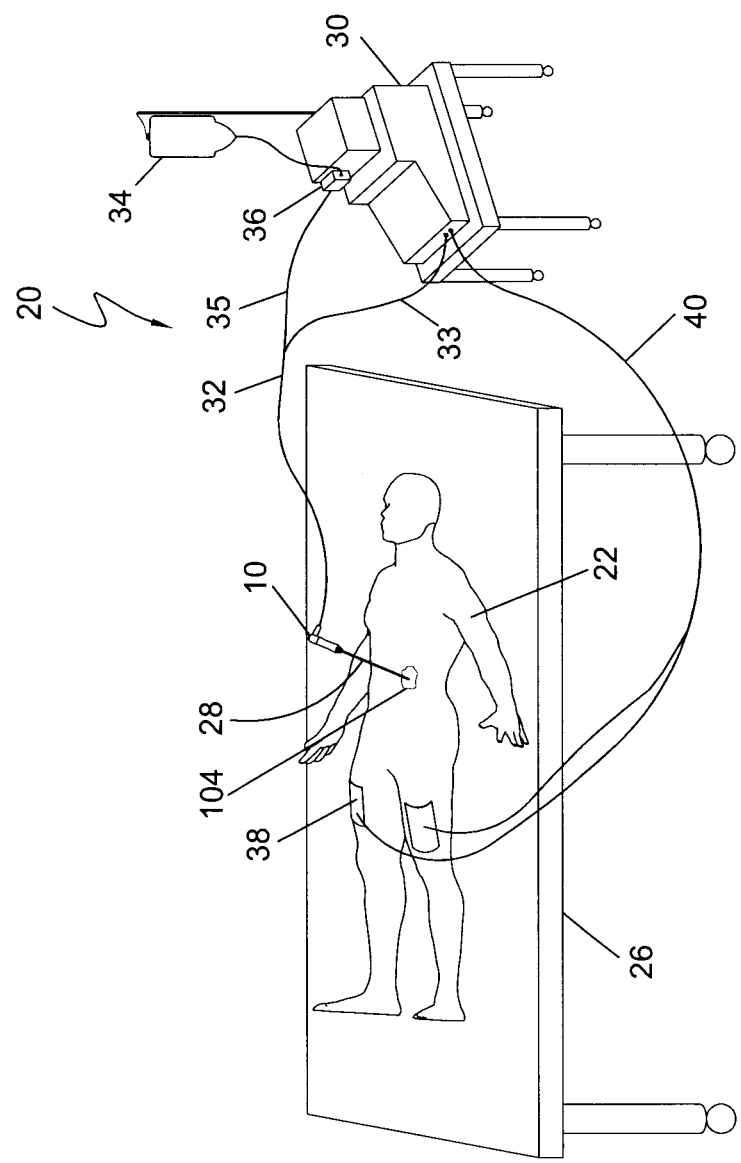
FIG. 1 illustrates certain components of a single-electrode ablation system embodying certain features of the present teachings.

Unless otherwise defined herein, scientific and technical terminologies employed in the present disclosure shall have the meanings that are commonly understood and used by one of ordinary skill in the art. As used herein and in the claims, the terms "at least one" and "one or more" have the same meaning and include one, two, three or more. The following terms, unless otherwise indicated, shall be understood to have the following meanings when used in the context of the present disclosure.

As used herein, "ultrasound imaging," "ultrasonic imaging," and "ultrasonography" all refer to medical imaging using an ultrasound source and an ultrasound detector.

As used herein, "biological imaging" includes any and all medical imaging, such as radiological imaging, endoscopy, thermography, medical photography, and microscopy. Non-limiting biological imaging techniques include ultrasonography, tomography (e.g., linear tomography, poly tomography, zonography, orthopantomography, computed tomography, contrast enhanced CT), magnetic resonance imaging (MRI), fluoroscopy, imaging using gamma cameras, positron emission tomography (PET), projection radiography (X-rays), diffuse optical tomography, elastography, electrical impedance tomography, optoacoustic imaging, optical coherence tomography, and scanning laser opthalmoscopy. Any one or a combination of two or more of such imaging techniques may be used during image-guided procedures when constant and continuous feedback to the operator during a procedure is required.

As used herein, "tumor" and "tumorous tissue" refer interchangeably to abnormal or uncontrolled growth of cells in or on a patient's body. "Tumorogenic tissue" refers to cells prone to undergo such abnormal or uncontrolled growth and develop into tumors. Liquid-form tumors include leukemias. Solid or semi-solid tumors typically have defined borders as determined by biological imaging techniques or histology.

As used herein, an "operator" is a person or a robotic assembly who uses the ablation devices for treatments (e.g., coagulation, ablation). The operator may be a physician, including a surgeon.

A "low-conductivity" material is one characterized as having an electrical conductivity of $10^{-4}$ mhos/m or less, such as $10^{-5}$ mhos/m or less, or $10^{-6}$ mhos/m or less, and preferably an electrically non-conductive material. Non-limiting examples include diamond, ceramics, oxides, carbides, certain polymers, dielectric materials, and any other materials that can function as an electrical insulator. The low-conductivity described herein is distinguished from thermal conductivity as understood by one of ordinary skill in the art. The low-conductivity material disclosed herein may have any thermal conductivity, and is not limited thereto.

As used herein, "RF" and "radio frequency" refer interchangeably to electromagnetic waves having a frequency in a range of 100 kHz to 1 MHz, such as medium frequency (300 kHz to 1 MHz), and include 350 kHz, 400 kHz, 450 kHz, 500 kHz, 550 kHz, 600 kHz, 650 kHz, 700 kHz, as well as a range between any two of such values. In comparison, microwave ablation uses electromagnetic waves ranging from 900 MHz to 3 GHz. One of ordinary skill in the art would understand that microwave energy is unsuitable for use with the ablation devices disclosed herein.

As used herein, "monopolar," "unipolar," and "single-electrode" refer interchangeably to ablation devices having only one ablating electrode positioned within or adjacent to a tissue of a patient targeted for ablation, with a counter-electrode positioned on a surface area of the patient's body, such on chest, back, arms, or legs.

"Polymer" or "polymeric" refers to a natural, recombinant, synthetic, or semi-synthetic molecule having in at least one main chain, branch, or ring structure two or more repeating monomer units. Polymers broadly include dimers, trimers, tetramers, oligomers, higher molecular weight polymer, adducts, homopolymers, random copolymers, pseudo-copolymers, statistical copolymers, alternating copolymers, periodic copolymer, bipolymers, terpolymers, quaterpolymers, other forms of copolymers, substituted derivatives thereof, and mixtures thereof, and narrowly refer to molecules having 10 or more repeating monomer units. Polymers can be linear, branched, block, graft, monodisperse, polydisperse, regular, irregular, tactic, isotactic, syndiotactic, stereoregular, atactic, stereoblock, single-strand, double-strand, star, comb, dendritic, and/or ionomeric, can be ionic or non-ionic, can be neutral, positively charged, negatively charged, or zwitterionic, and can be used singly or in combination of two or more thereof.

Other than in the operating examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values can be used.

"Formed from" and "formed of" denote open claim language. As such, it is intended that a member "formed from" or "formed of" a list of recited components and/or materials be a member comprising at least these recited components and/or materials, and can further include other non-recited components and/or materials.

Embodiments and examples provided herein, including those following "such as" and "e.g.," are considered as illustrative only of various aspects and features of the present disclosure and embodiments thereof, without limiting the scope of any of the referenced terms or phrases either within the context or outside the context of such descriptions. Any suitable equivalents, alternatives, and modifications thereof (including materials, substances, constructions, compositions, formulations, means, methods, conditions, etc.) known and/or available to one skilled in the art can be used or carried out in place of or in combination with those disclosed herein, and are considered to fall within the scope of the present disclosure. Throughout the present disclosure in its entirety, any and all of the one, two, or more features and aspects disclosed herein, explicitly or implicitly, following terms "embodiment", "embodiments", "example", "examples", "such as", "e.g.", and the likes thereof may be practiced in any combinations of two, three, or more thereof (including their equivalents, alternatives, and modifications), whenever and wherever appropriate as understood by one of ordinary skill in the art. Some of these examples are themselves sufficient for practice singly (including their equivalents, alternatives, and modifications) without being combined with any other features, as understood by one of ordinary skill in the art. Therefore, specific details disclosed herein are not to be interpreted as limiting, but merely as a basis for the claims and as a representative basis for teaching one skilled in the art to variously employ aspects and features of the present disclosure in virtually any appropriate manner.

II. Ablation Devices

FIG. 1 illustrates the setting in which an ablation system 20 constructed in accordance with at least certain aspects of the present teachings may be used for treating a patient 22. With patient 22 positioned on an operating table 26, an ablation electrode 28 of an ablation device 10 is inserted into a target tissue 104 (e.g., soft tissue). Electrode 28 is operably connected to a power source 30 (e.g., an RF generator such as RITA® 1500× from AnqioDynamics, Inc., Latham, NY) via an electric cable 33. Ablation device 10 may further be connected to a liquid reservoir 34 (e.g., containing infusion liquid for infusion via a lumen within electrode 28 prior to and/or during an ablation procedure, for example, to reduce tissue desiccation) via tubing 35 which may share, at least partially, a common conduit 32 with cable 33. The liquid in reservoir 34 may be supplied via tubing 35 into the lumen within electrode 28 by a pump 36 (e.g., Intelliflow® infusion pump from AnqioDynamics, Inc.). Operating in a monopolar configuration, electrode 28 constitutes the only ablation electrode in system 20, with one or more counter-electrodes 38 (e.g., dispersive electrodes, such as RITA® ThermoPad from AnqioDynamics, Inc.) placed on a surface area of the patient 22 (e.g., legs) and connected to power source 30 through adaptor cable 40.

Ablation device 10 and certain components therein are illustrated in FIGS. 2 and 3A-3D. Electrode 28 having a central (longitudinal) axis 52 is adapted at its distal end to a low-conductivity tip 58; the combination of the two forms the primary trocar. A major proximal portion of electrode 28 is covered by an insulating material, such as in the form of an insulative sleeve 60, which may coextend with the major proximal portion of the electrode 28 through an opening 74 (through bore) of a cap 72 into a handle 44. The insulating sleeve 60 and the tip 58 in combination define an exposed portion 57 of the electrode 28. Within the handle 44, a proximal end of the electrode 28 is fixedly mounted (anchored) to a plug 50, while the insulative sleeve 60 is fixedly mounted to a nut 64. The nut 64 has male threads 66 on a portion of its side that are complementary to female threads 68 (grooves) on the inner wall of a tubular member 70 of the handle 44. A gripping portion 46 extends at a right angle from the handle 44. A common conduit 32 further extends from the gripping portion 46, carrying cable 33 and tubing 35. Tubing 35 connects a lumen 27 (FIGS. 3A and 3B) of electrode 28 to pump 36 (FIG. 1). Optionally, one end of tubing 35 may be placed within lumen 27, adjacent to openings 56 (e.g., a pair of infusion holes) that are fashioned along the exposed portion 57 and promixal to a distal end 29 of the exposed portion 57, such that the fluid is easily delivered out of the lumen 27 through the openings 56 to the target tissue surrounding the exposed portion 57. Optionally, a thermal sensor (e.g., thermal coupler) carried on a distal end of another tubing (not shown) may be placed within lumen 27 along the exposed portion 57 (such as juxtaposed to a proximal end of the tip 58) for feeding temperature of the exposed portion 57 (same as or similar to that of the surrounding tissue) back to the power source 30 or a circuit therein. The tubing carrying the thermal sensor may be parallel to the fluid-carrying tubing 35 and coextensive over substantially the entire length of the electrode 28.

FIGS. 3A and 3B show electrode 28 as a hollow tube having a lumen 27. Alternatively, electrode 28 may be a solid rod. Electrode 28 may be fairly rigid (e.g., solid sheath or rod, better for penetrating into tissue) or substantially flexible (e.g., spring or tubing, better for maneuvering through tissue), or electrode 28 may contain different segments having different rigidity/flexibility. Electrode 28 may be formed of a conductive material, such as metals and alloys thereof (e.g., stainless steel or alloys thereof, titanium or alloys thereof). Electrode 28 may have an outer diameter of 3 French (1 mm) to 12 French (4 mm), such as 4 French, 5 French, 6 French, 7 French, 8 French, 9 French, 10 French, 11 French, or in a range between any two of such values. Electrode 28 may have a full length of between 10 cm to 30 cm, such as 15 cm, 25 cm, or in a range between any two of such values.

As seen in FIG. 3B, and in greater detail in FIGS. 9A-9G, one or more openings 56 communicating with the lumen 27 of the electrode 28 and the target tissue surrounding the exposed portion 57 may be fashioned along and/or around electrode 28, such as in proximity (or adjacent) to the distal end 29 of the electrode 28. Such openings 56 would allow one or more liquids (e.g., infusion liquids, supplied, for example, by the combination of the reservoir 34, the pump 36, and the tubing 35 as illustrated in FIG. 1) to be delivered to the surrounding target tissue.

Figure 9A:
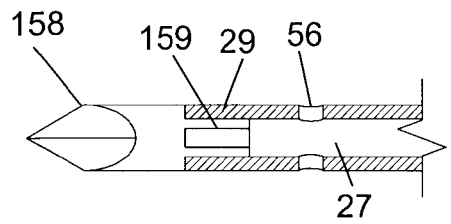
FIGS. 9A-9G illustrate different tip designs with respect to the exposed electrode portion.
Figure 9B:
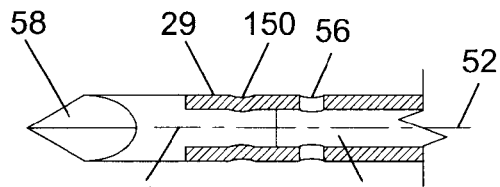
Figure 9C:
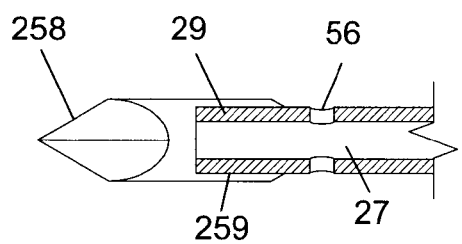
Figure 9D:
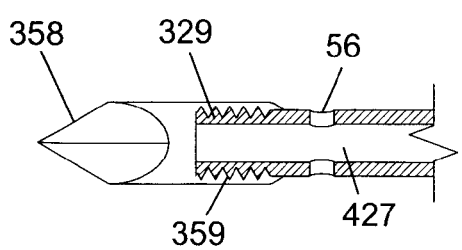
Figure 9E:
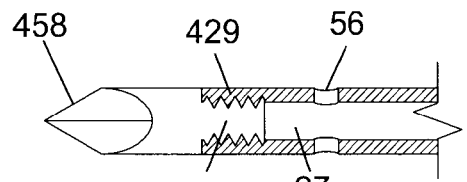
Figure 9F:
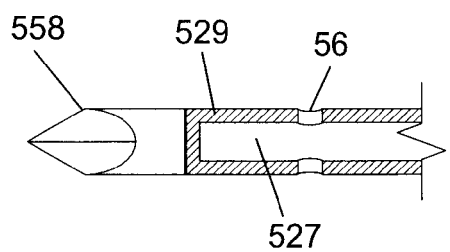
Figure 9G:
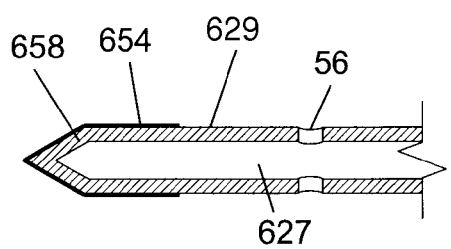

The distal end 29 of the electrode 28 may adjoin the low-conductivity, tissue piercing, tip 58 or at least a portion thereof, as shown by the various designs illustrated in FIGS. 3B and 9B. The pointed tip 58 may be formed of a polymer, such as any hard plastics (e.g., Teflon), ceramics, or other non-conductive materials (e.g., diamond, dielectric materials, oxides, carbides) that are sufficiently rigid for penetrating biological tissues. Non-limiting alternative designs of the tip are disclosed herein. In FIG. 9A, tip 158 has a hollow stem 159 adapted to be securely inserted into the lumen 27 of the electrode at its distal end 29, without obstructing the side openings 56. In FIG. 9B, tip 58 has a solid stem 59 adapted to be securey inserted into the lumen 27 of the electrode at its distal end 29 without obstructing the openings 56, where the electrode is crimped at 150 to prevent the tip 58 from disengaging the distal end 29 or moving along the central axis 52 of the electrode independently of the electrode. In FIG. 9C, tip 258 has a recess 259 for receiving the distal end 29 of the electrode snuggly therein, without covering up the openings 56. In FIG. 9D, tip 358 has a recess 359 with female threads therein that are complimentary to male threads on the distal end 329 of the electrode for secure engagement there between, leaving the openings 56 uncovered. In FIG. 9E, tip 458 has a stem 459 with male threads complimentary to female threads within the lumen 427 of the electrode at its distal end 429 for snuggle engagement there between, without obstructing the openings 56. In FIG. 9F, tip 558 is adhesively coupled to a closed distal end 529 of the electrode, such that the lumen 527 is separated from the tip 558. In FIG. 9G, electrode 628 is fashioned to have a closed pointed tip 658 as an integral part thereof (e.g., by tapering the distal end 629 into the tip 658), with a low-conductivity outer surface 654 implemented thereon (e.g., via anodization or coating with a low-conductivity material such as those disclosed herein) without obstructing the openings 56. There may be no gap present between any of the tips and the exposed portions of the electrodes to which they are coupled. The exposed surface of the tip and the exposed surface of the electrode may be linearly continuous with each other.

Figure 3C:
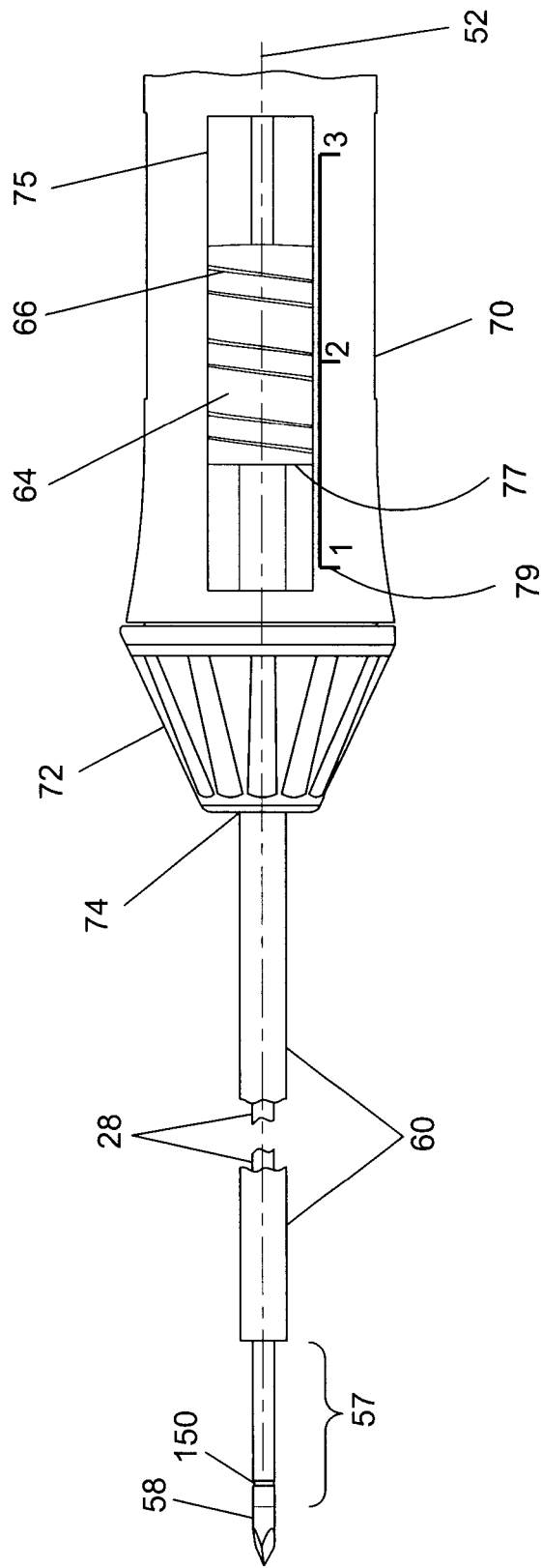
FIG. 3C illustrates indicia and at least one viewing window on a handle for determining the length of exposed portion of the electrode.
Figure 3D:
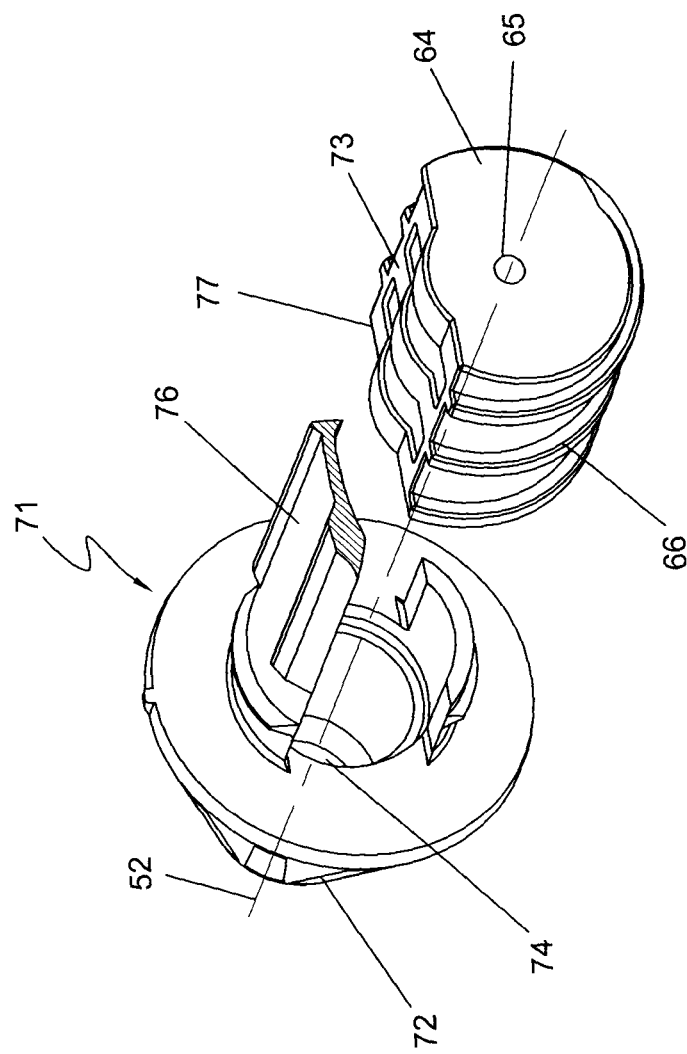
FIG. 3D illustrates a unitary piece including a cap and an arm in spatial relation to a nut.

As shown in FIG. 3A with reference to FIG. 3D, a proximal end 61 of insulative sleeve 60 is fixedly mounted within a through bore 65 of nut 64, through which the electrode 28 passes. Sleeve 60 is introduced into nut 64 from the distal edge 77 of the nut 64 and logged therein (e.g., using adhesive). The nut 64 is spirally rotatable along the electrode 28 and about the central axis 52 thereof, because the nut 64 with discontinuous male threads 66 is threadedly coupled to the tubular member 70 of the handle 44 having a continuous female thread 68 on its inner wall. The nut 64 is rotated by an arm 76 (driving blade) that is extended from or coupled to a cap 72 (nose cone). Optionally, the cap 72 and the arm 76 are two portions of an adjustment member 71 (shown in FIG. 3D as a unitary piece). The cap 72 has an opening 74 (through bore) at its distal end, through which the insulated proximal portion of electrode 28 passes, allowing the cap 72 carrying the arm 76 to freely rotate thereon. The arm 76 then in turn rotates the nut 64 by pushing against the longitudinal ledges 73 on the nut 64. Same or different materials may be used to construct the cap 72, the arm 76, the tubular member 70, and the nut 64. Non-limiting examples of suitable materials include metals and alloys thereof, ceramics, substantially rigid plastics (preferably fabricated through molding processes), and the likes thereof.

Figure 4:
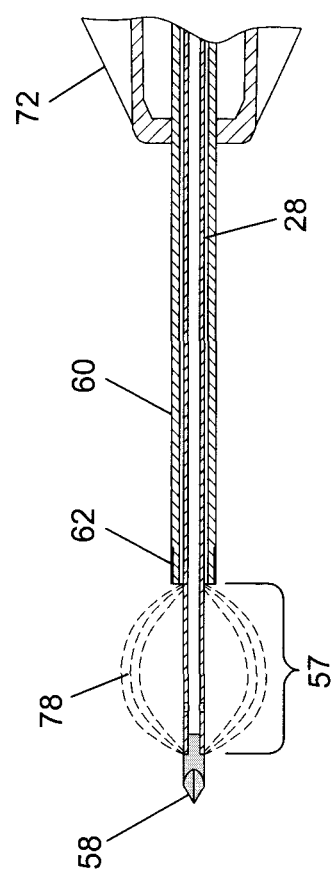
FIG. 4 illustrates the shape of the electric field provided by an exposed electrode portion sandwiched between a low-conductivity tip and an insulative sleeve.

The low-conductivity tip 58 and the proximal insulation 60 demarcate there between the exposed portion 57 of electrode 28 (FIG. 3C) for delivering RF energy to surrounding target tissue. The exposed portion 57 is adjustable as described herein, and has an operating length (axial dimension along axis 52) of between 0.1 cm and 10 cm, such as 0.5 cm, 1 cm, 1.5 cm, 2 cm, 2.5 cm, 3 cm, 3.5 cm, 4 cm, 5 cm, 6 cm, 8 cm, or in a range between any two of such values. In the presence of adjoining low-conductivity materials (e.g., those used to form the tip 58 and/or the sleeve 60) on both ends, the exposed portion 57 provides a substantially spheroidal (including oblate spheroidal, spherical, prolate spheroidal, ellipsoidal) electric field as indicated by lines 78 in FIG. 4, having the exposed portion 57 coincide with one of its axes of symmetry, with the field strength substantially equally concentrated at the two ends of the exposed portion 57, when electric pulses are applied thereto. With its diameter remaining the same, as the length of the exposed portion 57 increases, the electric field surrounding the exposed portion 57 would change in shape from oblate spheroidal to spherical to prolate spheroidal (e.g., ellipsoidal) to dumbbell-shaped.

Figure 6A:
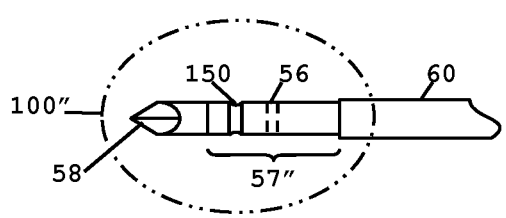
FIGS. 6A-6C illustrate the various ablation volumes anticipated from exposed electrode portions of various lengths.
Figure 6B:
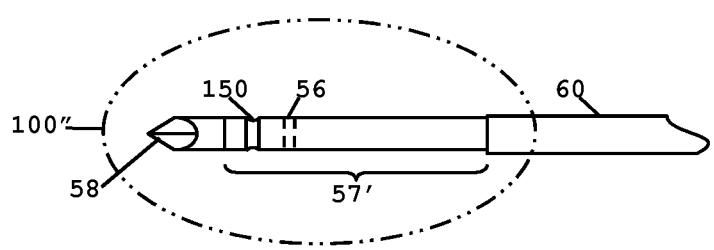
Figure 6C:
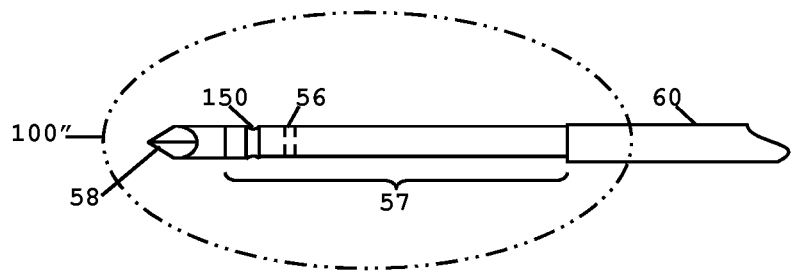

In one embodiment, spheroidal electric fields are chosen for creating ablation volumes that are more symmetric, such as being substantially spheroidal (e.g., spherical, ellipsoidal, superellipsoidal) or cylindrical (see FIGS. 6A-6C). Such ablation volumes exhibit substantial reflective symmetry with respect to the cross-sectional plane of symmetry of the exposed portion 57 that is orthogonal to the central axis 52. The adjustable length of the exposed portion 57 of electrode 28 and the predictable (and thus controllable) ablation geometry simplifies the ablation procedure while affording freedom of selecting the ablation volume and enhanced control of ablation volume by the operator. In one embodiment, the length of the exposed portion 57 is limited to no greater than the value at which the electric field just starts changing in shape from prolate spheroidal to dumbbell-shaped. As such, a ratio of the length of the exposed portion 57 to its outer diameter (of its cross-section) may be 80:1 or less, such as 60:1 or less, 50:1 or less, 40:1 or less, 30:1 or less, 20:1 or less, 15:1 or less, 10:1 or less, 7:1 or less, 5:1 or less, 3:1 or less, 1:1 or less, or in a range between any two of such values, such as between 25:1 and 6:1.

Figure 5:
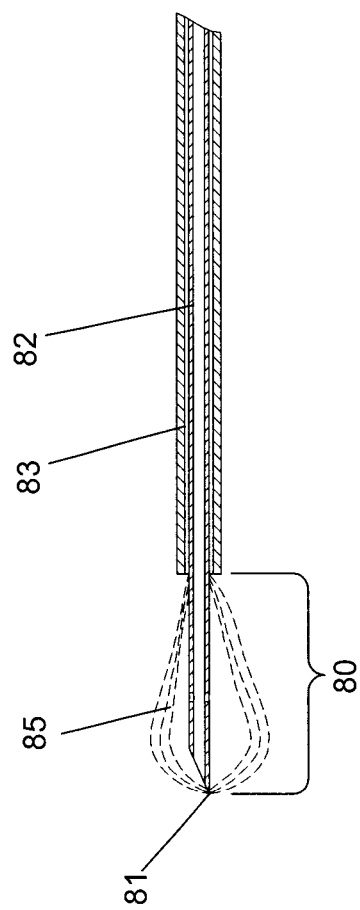
FIG. 5 illustrates the shape of the electric field provided by a needle electrode.

In comparison, as shown in FIG. 5, a needle electrode 82 having a proximal portion covered with insulation 83 but without the pointed tip 81 being rendered low-conductive, when powered with electric pulses, would provide a skewed ovoidal (e.g., teardrop-shaped or Q-tip-shaped) electric field as illustrated by lines 85 that is more concentrated at the pointed tip 81 (the focal point) than anywhere else along the exposed portion 80. Such an asymmetric electric field would result in ablation volumes without the desired symmetry and predictable volume. This would lead to either incomplete ablation of the targeted tissue, or unnecessary ablation of healthy tissue surrounding the targeted tissue, especially at the proximal end of the exposed portion 80.

The insulative sleeve 60 may be formed of a suitable polymer material, such as polyethylene, Teflon, PEEK, polyamides, and have a thickness of typically between 0.002 inches and 0.01 inches, such as between 0.005 inches and 0.008 inches. To facilitate direct visualization of the length of the exposed portion 57 using one or more biological imaging techniques (e.g., ultrasonography, tomography, MRI), the tip 58 and the sleeve 60, particularly portions thereof adjoining the exposed portion 57, may be constructed to enhance their contrast against the exposed portion 57, such as by chemical or mechanical means (e.g., surface roughening and/or gas bubble embedding) to modify their ultrasonic reflectivity, and/or by incorporating contrasting agents thereto (e.g., deposited thereon or doped therein). Such features are illustration by element 62 in FIGS. 3B, 4, 7B, 7C, 8A, and 8B. In one embodiment, the contrast agent includes a radio-opaque material, such as a barium salt or the like, such that the exposed portion 57 is visualized via electromagnetic imaging. Alternatively or in addition, the exposed portion 57 may be constructed to enhance its contrast against the tip 58 and the sleeve 60, such as by chemical or mechanical means (e.g., surface roughening and/or gas bubble embedding) to alter its ultrasonic reflectivity, and/or by incorporating contrasting agents therein.

Non-limiting examples of radio-opaque materials include metal powders, such as metrizamide, tantalum, tungsten, platinum, bismuth, and barium sulfate. Such materials may be used in the tip 58 and/or the sleeve 60 or portions thereof so long as they do not render the respective structures conductive. For example, the radio-opaque materials are not used to cover the surface of the tip 58 and/or the sleeve 60 or portions thereof, or used only on a small band at the proximal end of the tip 58 and/or the distal end of the sleeve 60. In one example, the tip 58 and/or the sleeve 60 or portions thereof is/are made from low-conductive materials doped with 5% or less (0.5-2%) by weight of a radio-opaque material, such as by mixing in the radio-opaque material during extrusion of a ceramic tip 58. Rough surfaces and gas-filled structures may be useful for ultrasonography. In some embodiments, the low-conductivity tip 58 and/or the insulative sleeve 60 or portions thereof are adapted to be imaged by both fluorography and ultrasonography.

With reference again to FIGS. 3A, 3C and 3D, the proximal end 61 of sleeve 60 is fixedly mounted to nut 64 within the through bore 65 therein. Sleeve 60 and nut 64 are threaded over electrode 28, and are jointly movable along the electrode 28 and jointly rotatable about the central axis 52. The nut 64 has a longitudinal cutaway, in the form of, for example, a slot or a recess, such as the one depicted in FIG. 3D, which bears longitudinal ledges 73. The longitudinal cutaway receives an arm 76 (e.g., a driving blade) that is juxtaposed thereto and is parallel to the central axis 52. When the arm 76 is rotated about the central axis 52, it pushes against the longitudinal ledges 73 so that the nut 64 rotates with the arm 76 about the central axis 52 in synchrony. Concomitantly, the nut 64 simultaneously glides linearly along the arm 76 and spirally along the electrode 28, while taking the sleeve 60 through the same motion. As seen clearly in FIG. 3D, the nut 64 has exterior helical threads 66 that are discontinuous (due to the cutaway) but parallel to each other. The threads 66 engage a continuous helical groove 68 of substantially complementary configuration (e.g., similarly pitched) formed in the inner wall of a hollow tubular member 70 of the handle 44 (FIGS. 2 and 3A), such that rotation of the nut 64 about the central axis 52 results in longitudinal movement of the nut 64 along the central axis 52. The tubular member 70 may be formed of a clear, thermoplastic or thermosetting, material that allows the position of the nut 64 or at least a distal edge 77 thereof within the tubular member 70 to be visible to the operator, for determining the length of the exposed portion 57 of the electrode 28 as described herein.

Figure 2:
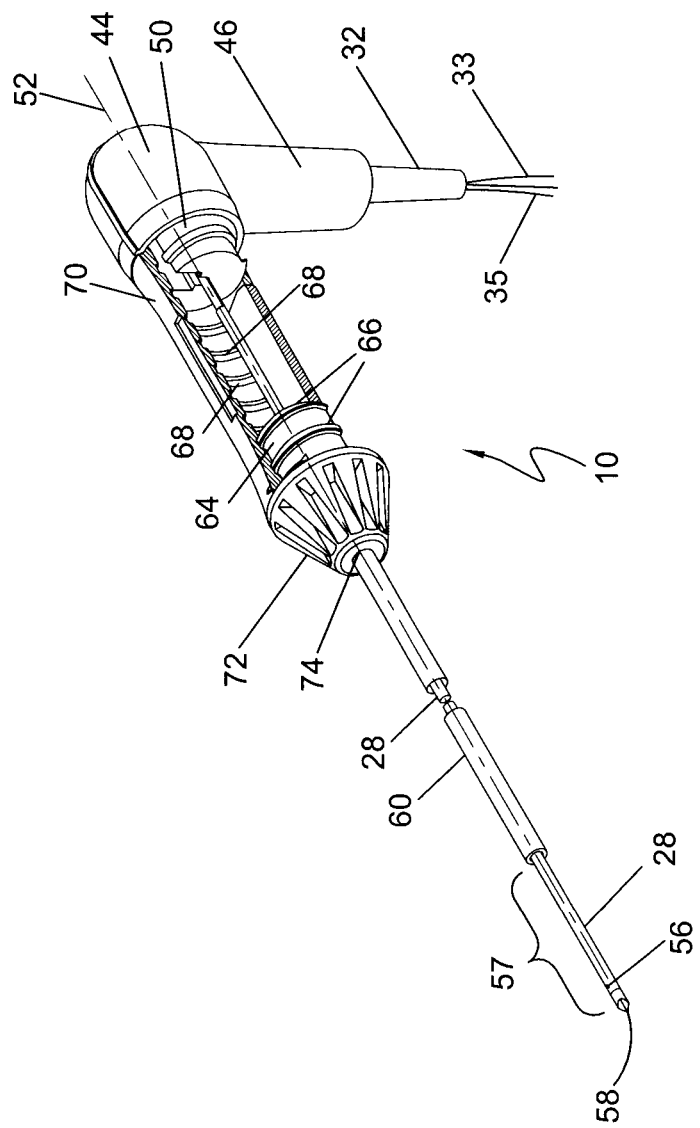
FIG. 2 is a perspective view of a single-electrode ablation device embodying certain features of the present teachings, with a partial cutout of the handle showing certain components and features therein.

Rotation of the arm 76 may be effected, for example, by rotating a knob or cap 72 mounted on the distal end of the tubular member 70 about the central axis 52 (FIG. 3A). In one embodiment, as shown in FIG. 3D, a unitary piece 71 serves as an adjustment member for rotating the nut 64, containing the cap 72 (nose cone) and the arm 76 (as a blade extending from the nose cone). The unitary piece 71 serves as a tuner for positioning the nut 64 and, subsequently, the insulative sleeve 60, along the electrode 28 with infinite precision. The cap 72 has an axial opening 74 at its distal end through which the electrode 28 and the sleeve 60 are coaxially received (FIG. 3A). The arm 76 extends over the unthreaded portion of the nut for rotation therewith. Thus, rotation of the cap 72 about the central axis 52 rotates the arm 76 about the central axis 52, which pushes nut 64 on either longitudinal ledges 73 that are parallel to axis 52, causing the nut 64 to spiral axially along the electrode 28, which then causes the sleeve 60 attached thereto to spiral axially along the electrode 28, thus adjusting the length (lengthening or shortening) of the exposed portion 57 of the electrode 28 (FIGS. 2, 3A, 3C, 3D). Cap 72 may be adjusted manually, by thumb and fingers, when the handle 44 is held in either of the operator's hands. Cap 72 may have features and/or textures fashioned on its outer surface for gripping and rotating. Cap 72 may be snapped into the tubular member 70 of the handle 44 without being fixedly mounted thereto, such that the cap can freely rotate about axis 52 without moving the tubular member.

As shown in FIG. 3C with reference to FIG. 2, tubular member 70 in the handle 44 may be transparent, as noted above, and/or may have a transparent or open window 75 along a portion or the entirety of its length, to allow the axial position of nut 64 or at least the distal edge 77 thereof to be visible to the operator. Further, the tubular member 70 may include indicia 79 alongside the window, such that values along the indicia 79 corresponding to the position of the distal edge 77 of the nut 64 is indicative of (e.g., equal to) the length of the exposed portion 57 of the electrode 28, or the total length of the exposed portion 57 in combination with the low-conductivity tip coupled thereto. Such a feature allows an operator to ablate a wide range of selected tissue volumes simply by setting the length of the exposed portion 57 of the ablating electrode 28 before and/or during the ablation procedure.

As disclosed herein, the length of the exposed electrode portion 57 is rendered adjustable by the insulative sleeve 60 and an insulation-adjustment mechanism. The adjustable insulative sleeve 60 can be spirally retracted or advanced along the length of the electrode 28, thereby changing the exposed length of the electrode 28. In this manner, the size and shape of the electric field surrounding the exposed electrode portion 57 can be tailored to the ablation volume within the target tissue.

FIGS. 6A-6C show the predictable ablation volumes produced in a monopolar-electrode RF ablation configuration using different exposed lengths of the ablation electrode. In all three figures, the tip 58, the crimp 150, the openings 56, and the insulation sleeve 60 are clearly labeled, while the exposed electrode portions of various lengths are labeled as 57'', 57', and 57, with their corresponding ablation volumes labeled as 100'', 100' and 100, respectively. The outlines of the ablation volumes 100'', 100', and 100 are general approximations of the actual ablation volumes, and are for illustration purpose only. In one practical scenario, the combined lengths of the exposed electrode portion 57 and the low-conductivity tip 58 are set to correspond roughly to the major axial dimension (length) of a selected volume to be ablated, which includes, for example, the target tumor tissue and an outer margin thereof (e.g., of 1 cm or less). The exposed electrode portion is inserted into the tumor along the major axis, such that RF energy delivered to the exposed electrode portion results in the ablation of the selected volume encompassing the tumor and its surrounding margin. Tailoring the size and shape of the electrical field and, consequently, the size and shape of the ablation volume, allows complete ablation of the undesired tissue without the need to repeatedly reposition (e.g., retracting & re-inserting) the ablation electrode, thus minimizing damages to surrounding healthy or non-tumorigenic tissue. It also allows a single ablation electrode to be used for ablating tumors of different sizes that would typically require the use of multiple ablation electrodes. In addition, the device allows the physician to select, in situ, with ease and accuracy, the active electrode length to match the tumor size, instead of having to guess the length required prior to placing the ablation electrode, resulting in either incomplete ablation or unnecessary damage to unintended tissues. By improving the level of accuracy in matching electrode length to tumor size, patient outcomes are improved by achieving a more complete ablation of the tumor. Also, the more precise size-matching allows the physician to more accurately place the electrode in small tumors and also near adjacent non-target tissue thereby avoiding unintentional ablation of healthy tissue and the complications that can arise from this error. It is noted that the ablation volume grows beyond (distal to) the distal end of the tip 58, as well as beyond (proximal to) the proximal end of the exposed electrode portion 57. Such growths may have a linear dimension along the central axis of the electrode of, for example, less than 5 mm, such as 2.5 mm or less.

As with the low-conductivity tip, all or part (especially the portion adjoining the exposed electrode portion) of the insulative sleeve can be radio-opaque to allow visualization by electromagnetic imaging modalities such as tomography and MRI, or provided with internal air bubbles or the like to increase visibility via ultrasonography. In this manner, an operator can monitor the location of the electrode in the body using the low-conductive tip and insulative sleeve to indicate the position and length of the exposed electrode during the procedure. Such visualization of the ablation electrode can be combined with one or more of any number of techniques for visualizing tumors. Alternatively or in combination, the electrode or portions thereof (especially the exposed portion or segments thereof) may also be rendered ultrasonically reflective (e.g., roughened surfaces, embedded air bubbles) or radio-opaque (e.g., with contrast agents disclosed herein). The contrast-enhanced portions or segments may be in the form of bands around the electrode.

The ablation devices presented herein are designed to be suitable for the biological imaging used during the ablation procedure, such as ultrasonography, tomography, and MRI. In one embodiment, the ablation device is designed to fit in a CT gantry. It is noted that substantially the entire tip 58 or at least a major distal portion thereof, with a dimension of, for example, 4 mm, may not be radio-opaque, thus not showing up under electromagnetic imaging such as CT-imaging.

The adjustment mechanism disclosed herein for adjusting the length of the exposed electrode portion allows the adjustment to be made before the electrode is inserted into the patient, or after the electrode reaches the target tissue (in situ). In this manner, an operator can estimate the length of the major axis of a tumor, preselect a corresponding electrode length, and then introduce the electrode into the body. Alternatively, an operator can insert the electrode into the body, and then adjust the length of the exposed electrode to match the major axis of the tumor. The latter method allows adjustment of the electrode length based on the information provided by a constant feedback source (e.g., real-time imaging using modalities such as ultrasonography, tomography, and MRI), and is well-suited for cases where the operator does not know the size or shape of the tumor until after the electrode insertion procedure has commenced.

Also as described herein, the ablation device may include an indicia (e.g., a linear scale) for indicating the exposed length of the electrode, or the exposed portion of the electrode plus the length of the low-conductivity tip. In one example, the scale indicates a length of from 1 cm to 3 cm, which allows the length of the electrode to be set anywhere in or around that range without the need to physically measure the length of the exposed electrode. Use of the built-in scale in the handle allows the length of the electrode to be accurately set while avoiding the need to bring measuring instruments in proximity to the electrode, which is typically sterile immediately prior to insertion into the body of the patient.

Any of the above-described embodiments of the presently disclosed ablation devices may be adapted to deliver liquid to the site of ablation. Such liquids may be isotonic, hypotonic, or hypertonic relative to the target tissue. The built-in infusion capability facilitates the cooling down of the ablating electrode after each ablation to stop or prevent unnecessary and/or excessive ablation, and to re-set the ablating electrode for the next ablation. In some embodiments, liquid infusion cools the tissue being ablated to avoid burning or charring and to prevent desiccation during an ablation operation. The liquid infusion may bathe the tissue(s) being ablated in a solution of uniform conductivity, thereby increasing the uniformity of the electric field at the ablation site. Increasing the uniformity of the electric field gives the operator more control over the shape and size of the ablation volume. The liquid may include one or more therapeutic agents or compositions for formulations thereof, such as for killing tumor cells, preventing metastasis, reducing angiogenesis, promoting healing, reducing infection, and reducing pain from treatment, but not limited thereto. The infusion liquid is delivered to the ablation device via tubing 35, which may share a common conduit 32 with the cable 33 that provides current to the ablating electrode 28 (FIG. 1).

III. Methods of Using the Ablation Devices

The ablation devices disclosed herein are used in general for necrotic destruction and/or removal of undesirable tissues and other matters of a mammalian patient. Such tissues and matters may be of any origin (e.g., endogenous, exogenous, grafted, implanted), type (e.g., benign, malignant, any tissue types, soft, hard), and physical state (e.g., liquid, gelatinous, viscous, semi-solid, solid). Non-limiting examples include tumors or cancers or other excessive growths of any tissue type that is benign or malignant (e.g., brain, eye, neural, skin, nasal, oral, head/neck, muscular, vascular, lymphatic, blood, mucosal, epithelial, esophageal, tracheal, lung, bone, cardiac, liver, pancreatic, kidney, prostate, breast, ovarian, uterine, cervical, colorectal, intestinal, stomach, bladder, urethral, adrenal, testicular, adipose, nerve), as well as cosmetically or aesthetically un-appealing tissues such as fat, skin, pigmentations, and varicosity.

Figure 7A:
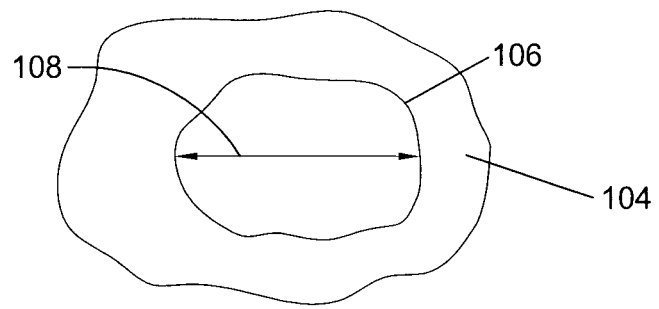
FIGS. 7A-7C illustrate steps in practicing an embodiment of the methods in which the length of the exposed portion of electrode is preset before inserting the electrode into a target tissue.
Figure 7B:
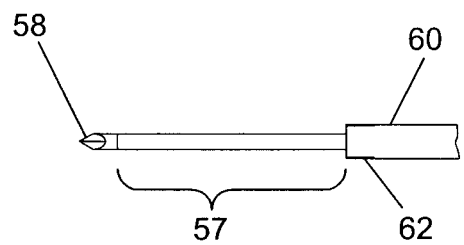
Figure 7C:
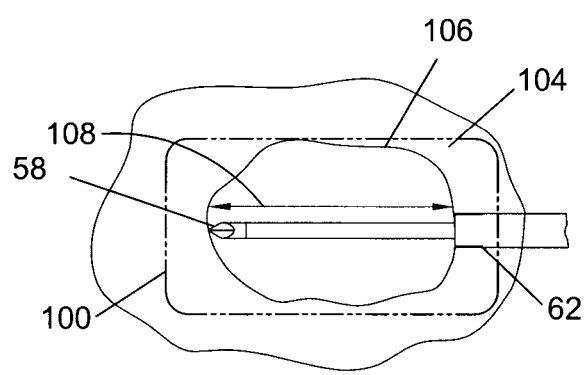

According to one method, the length of the exposed portion of electrode is adjusted prior to inserting the electrode into a target tissue 104, as illustrated in FIGS. 7A-7C. Adjustment may be accomplished using the sleeve adjustment mechanism in the handle, as described herein.

Specifically, an operator may first determine the length of the major axis of a selected ablation volume, such as one that is sufficient to encompass a tissue to be ablated (e.g., a tumor), by visualizing the target tissue using conventional biological imaging and/or other methods, such as ultrasonography, tomography, MRI, biopsy combined with histological analysis, and exploratory surgery. This step is illustrated in FIG. 7A, which shows an image of a target tissue 104 having a tumor 106 therein that is outlined by such visualization methods, the tumor 106 having a major axis dimension 108. The operator then adjusts the axial position of the insulative sleeve 60 to select a combined length of the exposed portion 57 and the tip 58 that approximates, or is longer than (to ensure complete ablation of tumor 106), the major axis dimension 108 of the tumor 106. Alternatively, the selected length may be shorter than the major axis dimension 108, so long as the selected ablation volume 100 sufficiently encompasses the tumor 106, with the expectation that tumor tissue extending past the electrode will also be ablated.

Once the length of exposed electrode 57 has been preset, the electrode is inserted into the target tissue, along the major axis dimension 108, until the combined length of the tip 58 and the exposed electrode portion 57 substantially superimposes on or sufficiently covers over the major axis dimension 108. Insertion and alignment may be accomplished using a constant feedback technique (e.g., real-time biological imaging methods). Following placement of the electrode, current is applied to the ablation electrode at a sufficient amount and/or over a sufficient duration to ablate the selected tissue volume 100.

According to another ablation method, the length of the exposed electrode portion is adjusted to match the selected tissue volume for ablation after the electrode is inserted into the target tissue, by in situ adjustment of length of the exposed electrode portion. The method is illustrated in FIGS. 8A and 8B, where the figure numbers employed in FIGS. 7A-7C are used to indicate analogous structures.

In a first step, illustrated in FIG. 8A, an operator introduces the electrode with a relatively short exposed electrode portion 57" into the target tissue 104, along the major axis dimension (not shown) of the to-be-ablated tissue 106, until the tip 58 reaches a distal boundary of the tissue 106. Then the operator may use the adjust mechanism that is outside the patient's body to retract the insulative sleeve 60 until the desired length of the exposed electrode portion 57 is reached, such that the combined length of the exposed portion 57 and the tip 58 that approximates, or is longer than (to ensure complete ablation of tumor 106), the major axis dimension 108 of the tumor 106. Alternatively, the selected length may be shorter than the major axis dimension 108, so long as the selected ablation volume 100 sufficiently encompasses the tumor 106, with the expectation that tumor tissue extending past the electrode will also be ablated. Verification of the adjustment may be achieved by reading the indicia on the handle that indicates the length of the ablation electrode being exposed. Alternatively or in combination, a constant feedback technique, such as real-time biological imaging, may be employed to direct visualize the lengthened exposed electrode portion, with optional aids of the contrasting features such as the ultrasonically reflective or radio-opaque band 62 on the insulative sleeve 60. Following placement of the electrode, current is applied to the ablation electrode at a sufficient amount and/or over a sufficient duration to ablate the selected tissue volume 100.

A software package, stored on a suitable storage medium (e.g., hard drive, compact disk, memory chip), may be implemented with the ablation system 20, such as installed in a computer that is coupled to at least the power source 30 and the ablation device 10 (FIG. 1). The software package may be used for default and/or modifiable parameter settings, for receiving and/or analyzing feedback signals, and/or for automated adjustments of operation parameters. For example, the default RF time may be set to 15 minutes. Within the RF energy delivery algorithm, the first temperature ramp may be set to 1.3° C./second, with a first ramp temperature set at 90° C., and the second temperature ramp may be set to 1° C./(37 seconds), with an endpoint temperature set to 103° C. The default RF energy may be set to 30 Watts. The default 30-second cool down temperature may be set to 60° C. or greater, such that if the actual cool down temperature is lower than 60° C., the operator may turn on the RF power for an additional 5 minutes.

While the methods are described in the alternative, one skilled in the art will appreciate that a combination of methods may also be used. For example, an operator may preselect the length of the electrode prior to insertion into the body, and then refine the adjustment once the electrode is positioned in the body. Alternatively, it may be desirable to place the insulative sleeve in the fully retracted or fully advanced position (or an intermediate position) to facilitate insertion of the device, and then adjust the exposed length of the electrode upon insertion.

One skilled in the art will recognize that the present ablation devices and methods are useful in ablating tissues of any regular or irregular shapes and sizes. In certain cases, the tissue to be ablated may not have its major axis dimension readily accessible for placing the electrode thereto. Ablation of such tissue areas can be accomplished by ablating about the tissue area, such that the combined volume of the selected ablation volumes encompasses the tissue area to be ablated. Thus, the present ablation device can be used to ablate irregular shaped tumors. It will also be recognized that the device may be used for ablating other tissue pathologies, e.g., benign ovarian tumors and cysts, and nervous tissue, as part of pain management.

Non-limiting examples correlating certain parameters of the ablation procedures and the certain parameters of the resulting ablation volume in soft tissues (e.g., liver), optionally with liquid infusion, are illustrated in following table, where (E) refers to the approximate length (in cm) of the exposed electrode portion, (T) refers to the approximate time duration (in minutes) of RF energy application, (L) refers to the approximate length (in cm) of the resulting ablation volume, and (W) refers to the approximate width (in cm) of the resulting ablation volume.

| (E) | (T) | (L) | (W) |
|---|---|---|---|
| 1   | 1.5 | 1   | 1   |
| 1.5 | 1.5 | 1.5 | 1   |
| 2   | 2.5 | 2   | 1   |
| 2   | 3.5 | 2.5 | 1   |
| 2.5 | 4   | 3   | 1   |
| 1   | 4.5 | 1.5 | 1.5 |
| 1.5 | 4   | 2   | 1.5 |
| 2   | 5.5 | 2.5 | 1.5 |
| 2.5 | 5   | 3   | 1.5 |
| 1.5 | 7.5 | 2   | 2   |
| 2   | 9   | 2.5 | 2   |
| 2.5 | 9   | 3   | 2   |
| 2.5 | 15  | 3   | 2.5 |

The foregoing description of the embodiments of the present invention has been provided for the purposes of illustration and description. It is not intended to be exhaustive or to limit the invention to the precise embodiments disclosed. Many modifications and variations will be apparent to those skilled in this art. It is intended that the scope of the invention be defined by the following claims and their equivalents.

It is claimed:

1. An ablation device for ablating a selected tissue volume in a patient, comprising:
    an electrode having a central axis,
    an insulative sleeve coaxially adapted over a portion of the electrode and rotatable about the central axis,
    a nut through which the electrode passes, wherein the insulative sleeve is fixedly mounted to the nut and wherein the nut is rotatable along the electrode about the central axis, and
    an adjustment member through which the electrode passes, the adjustment member being movably coupled to the nut through an arm, and the nut being rotatable about the central axis, wherein: rotation of the adjustment member about the central axis is capable of rotating the nut about the central axis and consequently moving the sleeve along the electrode.

2. The device of claim 1, wherein the sleeve comprises a proximal end and a distal end such that the distal end of the sleeve alone the electrode is axially adjustable along a length of the electrode for selection of different ablation volumes.

3. The device of claim 1, further comprising a handle to which the adjustment member is coupled, and in which the nut is positioned, wherein the handle is transparent or comprises at least one window through which at least a portion of the nut is visible.

4. The device of claim 3, wherein the handle further comprises indicia for identifying an axial length of a portion of the electrode not covered by the sleeve.

5. The device of claim 1, wherein the electrode has one or more openings along the exposed portion for delivery of fluid to the target tissue.

6. The device of claim 1, wherein: the exposed portion is ultrasonically reflective or radio-opaque, or a distal end of the sleeve is ultrasonically reflective or radio-opaque.

7. The device of claim 1, wherein the ablation area of the selected tissue is substantially spheroidal.

* * * * *